United States Patent
Kodama et al.

(10) Patent No.: US 9,206,415 B2
(45) Date of Patent: Dec. 8, 2015

(54) ANTI-APOPTOSIS OR ANTI-NECROSIS INDUCTION METHOD

(75) Inventors: Shohta Kodama, Fukuoka (JP); Tomoyuki Godai, Kobe (JP)

(73) Assignees: FUKUOKA UNIVERSITY, Fukuoka (JP); MAYATEC CO., LTD., Hyogo (JP)

(*) Notice: Subject to any disclaimer, the term of this patent is extended or adjusted under 35 U.S.C. 154(b) by 43 days.

(21) Appl. No.: 13/993,832

(22) PCT Filed: Jan. 18, 2012

(86) PCT No.: PCT/JP2012/000252
§ 371 (c)(1),
(2), (4) Date: Jul. 10, 2013

(87) PCT Pub. No.: WO2012/098864
PCT Pub. Date: Jul. 26, 2012

(65) Prior Publication Data
US 2013/0316429 A1 Nov. 28, 2013

(30) Foreign Application Priority Data
Jan. 19, 2011 (JP) .................................. 2011-008828

(51) Int. Cl.
*C12N 13/00* (2006.01)
*C12N 5/077* (2010.01)
*A61N 1/32* (2006.01)

(52) U.S. Cl.
CPC .............. *C12N 13/00* (2013.01); *C12N 5/0656* (2013.01); *A61N 1/32* (2013.01); *C12N 2529/00* (2013.01)

(58) Field of Classification Search
CPC ...................................................... C12N 13/00
See application file for complete search history.

(56) References Cited

U.S. PATENT DOCUMENTS

| 5,387,231 A | * | 2/1995 | Sporer ........................... 607/48 |
| 8,290,581 B2 | | 10/2012 | Kriksunov et al. |

FOREIGN PATENT DOCUMENTS

| CN | 2721133 Y | 8/2005 | |
| CN | 101878053 A | 11/2010 | |
| DE | EP1337625 * | 7/2004 | ............... C12N 5/06 |
| JP | 2004305046 | 11/2004 | |
| WO | 9823326 A1 | 6/1998 | |
| WO | 2008096631 A1 | 8/2008 | |

OTHER PUBLICATIONS

Picker et al. (Low-Volt Pulsed Micro-Amp Stimulation. Document Created 2003).*
Sugimoto et al. (Optimum microcurrent stimulation intensity for galvanotaxis in human fibroblasts, Journal of Wound Care, vol. 21, Issue 1, Jan. 11, 2012, pp. 5-11).*
Yu Gang, Dong Wei-Wei, Luo Yong, et al.; "Modern Rehabilitation", The First Affiliated Hospital of Chongqing University of Medical Sciences, China Academic Journal electronic Publishing House., Jan. 2001, vol. 5, No. 1, p. 60, Sections 1.3 of Abstract; p. 61, Section 3 of Discussion.
Guangqin Li et al, "Effect of Fastigial Nucleus Stimulation on anti-apoptotic protein with cerebral infarction", Department of Neurology, 1st Hospital, chongqing Medical University, Chongqing, vol. 11, Issue 5, pp. 271 and 272.

* cited by examiner

*Primary Examiner* — Karen Cochrane Carlson
*Assistant Examiner* — Natalie Moss
(74) *Attorney, Agent, or Firm* — The Ollila Law Group LLC

(57) ABSTRACT

Disclosed herein is a method for simply inducing an anti-apoptotic effect and/or an anti-necrotic effect in a living cell with good control without administering any drug. The method includes applying an alternating-current voltage to the living cell so that an electric current of 25 µA or higher but 75 µA or lower flows to induce an anti-apoptotic effect and/or an anti-necrotic effect in the living cell. The living cell used may be a cultured cell. The alternating-current voltage may be applied to a stage member on which a container holding the living cell is placed.

4 Claims, 1 Drawing Sheet

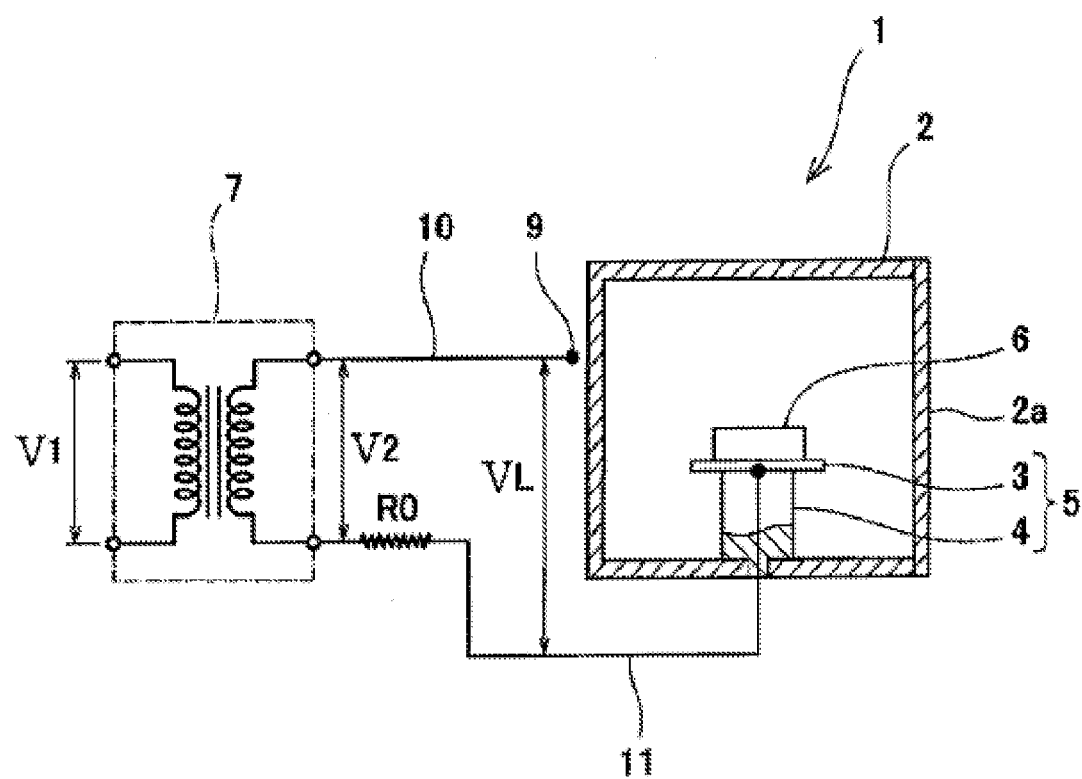

ANTI-APOPTOSIS OR ANTI-NECROSIS INDUCTION METHOD

TECHNICAL FIELD

The present invention relates to a method for inducing an anti-apoptotic effect and/or an anti-necrotic effect in a living cell.

BACKGROUND ART

A technique to suppress the oxidation of coffee or to maintain the freshness of vegetables is conventionally known in which an alternating-current voltage of 10 V or higher but 5 kV or lower is applied to an object to be treated so that an extremely weak electric current of 1 μA or higher but 1000 mA or lower flows (see Patent Documents 1 and 2). However, the mechanism remains unclear by which the oxidation of food can be suppressed or the freshness of food can be maintained by an extremely weak electric current.

Meanwhile, apoptosis is one mode of death of cells constituting a body of a multicellular organism, and is known as active cell suicide, that is, programmed cell death induced to keep individuals in better conditions. On the other hand, cell death induced by deterioration of an intracellular or extracellular environment such as poor circulation or external injury is known as necrosis. It is known that in order to suppress such apoptosis and necrosis, various drugs are administered to a living cell to induce an anti-apoptotic effect or an anti-necrotic effect. However, the fact that an anti-apoptotic effect or an anti-necrotic effect is induced by applying an electric current, which is a physical stimulus, to a living cell is not conventionally known at all.

Patent Document 1: JP-A-2004-305046
Patent Document 2: WO 2008/096631

SUMMARY OF THE INVENTION

Problems to be Solved by the Invention

Under the circumstances, it is an object of the present invention to provide a method for simply inducing an anti-apoptotic effect and/or an anti-necrotic effect in a living cell with good control without administering any drug.

Means for Solving the Problems

The present inventors have studied the influence of an extremely weak electric current on a living cell, and unexpectedly have found that an anti-apoptotic effect and/or an anti-necrotic effect are/is induced in a living cell at a very low electric current value within a certain range. This finding has led to the completion of the present invention.

More specifically, the present invention relates to a method for inducing anti-apoptosis and/or anti-necrosis in a living cell by applying an alternating-current voltage to the living cell so that an electric current of 25 μA or higher but 75 μA or lower flows.

In the present invention, the living cell used may be a cultured cell. Further, the voltage value of the alternating-current voltage is preferably 10 V or higher but 5 kV or lower.

More specifically, the present invention can be carried out by applying the alternating-current voltage to a stage member on which a container holding the living cell is placed.

Effects of the Invention

According to the present invention, it is possible to simply induce an anti-apoptotic effect and/or an anti-necrotic effect in a living cell with good control without administering any drug.

BRIEF DESCRIPTION OF THE DRAWINGS

FIG. 1 is a schematic diagram showing a structure of an alternating-current voltage applying device usable in one embodiment of the present invention.

MODE FOR CARRYING OUT THE INVENTION

FIG. 1 is a schematic diagram showing a structure of an alternating-current voltage applying device usable in one embodiment of the present invention. The alternating-current voltage applying device 1 has a treatment chamber 2. This treatment chamber may be a hermetically-sealable culture apparatus used for conventional cell culture. The culture apparatus is capable of maintaining its internal temperature and humidity at constant levels to culture cells. The treatment chamber 2 has a box-like shape and its wall section is made of a conductive material. In part of the wall section of the treatment chamber 2, a door 2a is provided through which a container 6 holding a living cell is transferred into or from the treatment chamber 2.

Inside the treatment chamber 2, a holder 5 is provided. The holder 5 includes, for example, a supporting member 4 made of an electrical insulating material and provided so as to stand on the bottom surface of the treatment chamber 2 and a plate-like stage member (table) 3 made of a conductive material and provided at the end of the supporting member 4. The container 6 is placed on the stage member 3. The container 6 is usually a vessel having a recess in its top surface, and a living cell is contained and held in the recess. As the container 6, a glass or resin dish for holding a living cell is usually used.

The alternating-current voltage applying device 1 has an electric transformer 7, and one terminal 9 of a pair of secondary output lines of the electric transformer 7 is insulated and is not connected to anywhere. In this way, in this embodiment, an output terminal on the side opposite to the side where a voltage is applied to the container 6 is insulated, and therefore a load impedance is smaller as compared to a case where the output terminal is opened, which makes it possible to reduce the output voltage of the electric transformer 7. Further, the other of the pair of secondary terminals of the electric transformer 7 is connected through a wiring 11 having a safety resistor R0 to the stage member 3 of the holder 5 provided in the treatment chamber 2. The wiring 11 is appropriately electrically insulated from the wall section of the treatment chamber 2. A primary voltage V1 can be regulated by a voltage operating unit (not shown), which makes it possible to regulate a load voltage VL to be applied to the container 6.

Hereinbelow, a description will be given of a method for holding a living cell and inducing an anti-apoptotic effect and/or a necrotic effect by applying an extremely weak electric current to the living cell with the use of the alternating-current voltage applying device having such a structure as described above.

First, the door 2a of the treatment chamber 2 is opened to place the container 6 holding a living cell on the stage member 3 of the holder 5, and then the door 2a is closed.

Then, the primary voltage V1 is applied across a pair of primary terminals of the electric transformer 7. Here, this primary voltage V1 is a sinusoidal alternating-current voltage with a commercial frequency. As a result, a secondary voltage V2 is induced across the secondary terminals of the electric transformer 7, and the load voltage VL, which is determined by deducting a voltage drop caused by the safety resistor R0 from the secondary voltage V2, is applied to the container 6. The container 6 and the insulated terminal 9 are insulated from each other by the supporting member 4 and air between the secondary terminals, and therefore a load current is applied to a secondary circuit of the electric transformer 7 and then to the container 6 depending on the load impedance (leak resistance or capacitance) between the container 6 and air between the secondary terminals. This load current is extremely weak. This is because the load impedance between the container 6 and air between the secondary terminals is very large. Then, the occurrence of apoptosis and/or necrosis is suppressed in the living cell held in the container 6 by this extremely weak load current.

The present invention is characterized by using an extremely weak electric current. In addition, an anti-apoptotic effect and/or an anti-necrotic effect can be induced in a living cell at a load current value within a very narrow range of 25 µA or higher but 75 µA or lower. Most preferably, the load current value is about 50 µA (40 µA to 60 µA).

Further, the present invention uses an alternating-current voltage. An anti-apoptotic effect and/or an anti-necrotic effect cannot be induced by a direct-current voltage.

The time during which an electric current is applied to induce an anti-apoptotic effect and/or an anti-necrotic effect is not particularly limited. Even when the current application time is short, a reasonable effect can be obtained, but the current application time is preferably 12 hours or longer, more preferably 24 hours or longer. However, if the current application time is too long, there is a fear that apoptosis or necrosis is adversely induced. For this reason, the current application time is preferably, for example, 48 hours or shorter.

A living cell usable in the present invention is not particularly limited. For example, living cells collected from multicellular organisms such as mammals (e.g., humans, mice, rats) and birds can be used. The living cell used may be one cultured under normal culture conditions.

The culture conditions are not particularly limited, either. Appropriate temperature, humidity, atmosphere, liquid culture medium, and additive may be selected depending on the type of living cell used. According to the present invention, as described above, an anti-apoptotic effect and/or an anti-necrotic effect can be appropriately induced by applying an extremely weak electric current while cultured cells are cultured under normal conditions.

EXAMPLES

Hereinbelow, the present invention will be described in more detail with reference to examples, but is not limited to these examples.
Materials and Methods
  (1) Cells
  In the following tests, commercially-available mouse-derived cells NIH3T3 (ATCC, Manassas, Va.) were used as cultured cells. The cells stored in a frozen state were thawed, subcultured to the fifth generation to stabilize cell growth, and then subjected to the tests.
  (2) Culture Environment
  The fifth-generation NIH3T3 cells ($2 \times 10^7$ cells/dish) were placed in a 60 mm cell culture dish (BD Bioscience, Bedford, Mass.) together with 10% fetal bovine serum, 1% antibiotic and antimycotic, and liquid cell culture medium, and cultured to about 80% confluency as determined when the maximum cell growth achievable in the dish was defined as 100% confluency.

The cell culture was performed in a tissue/cell incubator manufactured by Thermo. In this incubator, an electrically-insulating supporting member was placed, and a conductive stage member was further provided on the supporting member. The dish was allowed to stand on the stage member, and the stage member was connected to depak manufactured by Santetsu Engineering Inc. as the above-described electric current applying device.

The cells were cultured under conditions of a temperature of 37° C., a carbon dioxide concentration of 5%, and a humidity of 100% from start to finish irrespective of whether or not an electric current was applied. Further, the connection of the electric current applying device to the stage member in the incubator was performed with the utmost caution, and a detector VoltAlert (Fluke, Japan, www.fluke.com) was used to frequently make sure that there was no interference in a current-carrying region.

Then, the cells under test were divided into four groups depending on different set electric current values of the electric current applying device of 0 µA (no electric current was applied), 25 µA, 50 µA, and 75 µA, and the cells of each group were cultured while an electric current was applied at a voltage set to 10 V to 10000 V for 24 hours accurately. After the application of an electric current, the cultured cells were quickly washed with a washing liquid at 4° C. three times, physically separated from the culture dish using a cell scraper (Fisher Scientific, Pittsburgh, Pa.), and collected in a microcentrifuge tube. After the completion of centrifugation at 4° C., a supernatant was removed and mRNA was extracted from the cells of each group and weighed.

(3) Extraction of mRNA and Examination of Anti-Apoptosis-Related Genes by PCR Array (Verification of Anti-Apoptotic Effect)

The mRNA of each group was purified by a spin column method using a spin column (QIAGEN Inc., Valencia, Calif.). Then, 10 ng of the mRNA was transcribed to cDNA, and the cDNA was used to perform a search for 84 kinds of apoptosis-related genes by a semi-quantitative PCR array (SuperArray Bioscience, Frederick, Md.).

The expression of each of the genes was quantified by determining how much more highly the gene was expressed in each of the groups other than the 0 µA control group (to which no electric current was applied) than in the control group, and the results are shown in Tables 1 and 2.

TABLE 1

| | Test Sample/Control | | |
|---|---|---|---|
| Gene Names | 25 µm/0 µm | 50 µm/0 µm | 75 µm/0 µm |
| Akt1 | 0.921 | 1.054 | 0.874 |
| Apaf1 | 1.166 | 0.886 | 0.911 |
| Api5 | 0.988 | 1.289 | 1.054 |
| Atf5 | 1.073 | 1.106 | 1.040 |
| Bad | 1.030 | 1.138 | 1.047 |
| Bag1 | 1.142 | 1.138 | 1.138 |
| Bag3 | 1.015 | 1.091 | 1.004 |
| Bak1 | 0.974 | 1.004 | 0.937 |
| Bax | 1.022 | 1.091 | 1.047 |
| Bcl10 | 0.733 | 2.743 | 1.410 |
| Bcl2 | 0.759 | 0.793 | 0.658 |
| Bcl2l1 | 1.096 | 1.236 | 1.084 |
| Bcl2l10 | 0.185 | 0.456 | 0.453 |
| Bcl2l2 | 1.058 | 0.950 | 0.937 |
| Bid | 0.860 | 0.990 | 0.918 |
| Naip1 | 0.298 | 0.264 | 0.220 |

TABLE 1-continued

|  | Test Sample/Control | | |
| --- | --- | --- | --- |
| Gene Names | 25 μm/0 μm | 50 μm/0 μm | 75 μm/0 μm |
| Naip2 | 0.921 | 0.950 | 0.984 |
| Birc2 | 1.081 | 1.280 | 1.106 |
| Birc3 | 1.037 | 1.099 | 1.091 |
| Xiap | 1.166 | 1.069 | 1.018 |
| Birc5 | 0.684 | 0.761 | 0.777 |
| Bnip2 | 1.081 | 1.076 | 1.011 |
| Bnip3 | 1.103 | 1.114 | 1.091 |
| Bnip3l | 1.081 | 1.091 | 1.040 |
| Bok | 0.988 | 0.880 | 0.880 |
| Card10 | 0.718 | 0.788 | 1.410 |
| Nod1 | 1.096 | 1.069 | 1.186 |
| Card6 | 1.081 | 1.138 | 1.122 |
| Casp1 | 0.872 | 0.577 | 0.804 |
| Casp12 | 0.974 | 1.106 | 1.146 |
| Casp14 | 1.882 | 1.186 | 1.874 |
| Casp2 | 1.008 | 1.084 | 1.047 |
| Casp3 | 0.915 | 1.069 | 0.839 |
| Casp4 | 0.791 | 1.130 | 1.061 |
| Casp6 | 1.051 | 1.228 | 1.153 |
| Casp7 | 0.775 | 1.254 | 1.004 |
| Casp8 | 0.903 | 1.271 | 1.084 |
| Casp9 | 1.037 | 1.170 | 1.178 |
| Cflar | 0.903 | 1.076 | 0.977 |
| Cidea | 1.081 | 1.186 | 1.186 |
| Cideb | 1.037 | 1.186 | 1.219 |
| Cradd | 1.340 | 1.254 | 1.178 |
| Dad1 | 1.466 | 1.245 | 0.957 |

TABLE 2

| Dapk1 | 1.303 | 1.401 | 1.061 |
| --- | --- | --- | --- |
| Dffa | 1.044 | 1.219 | 0.990 |
| Dffb | 1.030 | 1.186 | 0.963 |
| Tsc22d3 | 1.037 | 1.054 | 1.032 |
| Fadd | 1.081 | 1.032 | 0.943 |
| Fas | 0.961 | 1.450 | 1.430 |
| Fasl | 1.081 | 1.186 | 1.186 |
| Hells | 437.155 | 510.582 | 400.595 |
| Il10 | 4.234 | 1.724 | 0.614 |
| Lhx4 | 0.903 | 2.152 | 0.705 |
| Ltbr | 0.884 | 1.025 | 1.004 |
| Mcl1 | 1.066 | 1.228 | 1.153 |
| Nfkb1 | 1.174 | 1.047 | 1.186 |
| Nme5 | 1.550 | 2.542 | 2.473 |
| Nol3 | 1.127 | 1.091 | 1.178 |
| Pak7 | 1.081 | 1.186 | 1.186 |
| Pim2 | 1.001 | 1.122 | 1.069 |
| Polb | 1.037 | 1.186 | 1.122 |
| Prdx2 | 1.096 | 1.211 | 1.162 |
| Pycard | 1.416 | 0.997 | 1.245 |
| Ripk1 | 1.008 | 1.130 | 1.114 |
| Rnf7 | 1.199 | 1.254 | 1.236 |
| Sphk2 | 0.981 | 1.047 | 0.997 |
| Tnf | 1.081 | 1.186 | 1.186 |
| Tnfrsf10b | 1.142 | 1.262 | 1.219 |
| Tnfrsf11b | 0.961 | 1.084 | 1.011 |
| Tnfrsf1a | 0.961 | 1.047 | 1.054 |
| Cd40 | 1.081 | 1.186 | 1.186 |
| Tnfsf10 | 1.073 | 1.122 | 0.640 |
| Tnfsf12 | 1.051 | 1.114 | 1.130 |
| Cd40lg | 1.081 | 1.186 | 1.186 |
| Cd70 | 1.081 | 1.186 | 1.186 |
| Traf1 | 0.860 | 0.868 | 0.804 |
| Traf2 | 0.928 | 1.011 | 1.018 |
| Traf3 | 1.015 | 1.091 | 1.114 |
| Trp53 | 1.037 | 1.032 | 1.025 |
| Trp53bp2 | 1.008 | 1.018 | 0.937 |
| Trp53inp1 | 1.001 | 1.138 | 0.957 |
| Trp63 | 0.308 | 0.581 | 0.334 |
| Trp73 | 1.895 | 1.491 | 0.542 |
| Zc3hc1 | 1.073 | 1.186 | 1.153 |
| Gusb | 0.860 | 0.918 | 1.032 |
| Hprt1 | 0.872 | 0.950 | 0.821 |

TABLE 2-continued

| Hsp90ab1 | 1.037 | 1.018 | 1.091 |
| --- | --- | --- | --- |
| Gapdh | 1.088 | 1.004 | 0.984 |
| Actb | 1.183 | 1.122 | 1.099 |

The genes whose expression was 1.5 times or more that in the control group were regarded as genes whose expression was increased and the genes whose expression was less than 0.40 times that in the control group were regarded as genes whose expression was decreased. The genes whose expression was increased or decreased are as follows.

Bcl10 (which shows an anti-apoptotic effect when its expression is increased)

Bcl2/10 (which shows an apoptotic effect when its expression is decreased)

Naip1 (which shows an apoptotic effect when its expression is decreased)

Casp14 (which shows an apoptotic effect when its expression is increased)

Hells (which shows an anti-apoptotic effect when its expression is increased)

IL10 (which shows an anti-apoptotic effect when its expression is increased)

Lxh4 (which shows an anti-apoptotic effect when its expression is increased)

Nme5 (which shows an anti-apoptotic effect when its expression is increased)

Trp63 (which shows an apoptotic effect when its expression is increased)

As can be seen from the above results, the expression of the genes showing an anti-apoptotic effect (especially, Bcl10, Hells, Lxh4, and Nme5) was enhanced in the groups to which an extremely weak electric current of 25 to 75 μA was applied. That is, it was demonstrated that an anti-apoptotic effect is induced by the application of an electric current. Particularly, the expression of the genes showing an anti-apoptotic effect was significantly enhanced in the group to which an extremely weak electric current of 50 μA was applied, and therefore it was found by a molecular biological technique that an optimum value of an extremely weak electric current applied to NIH3T3 cells for 24 hours is 50 μA.

(4) Verification of Anti-Necrotic Effect by Histological Staining (Chamber-Assay Method)

4-1) AnnexinV×PI Staining

NIH3T3 cells were grown in a chamber by the above-described culture method and costained with AnnexinV (green) for detecting apoptotic cell membrane and Propidium Iodido (PI) (red) for detecting necrotic cells. The NIH3T3 cells were divided into four groups depending on different set electric current values of the electric current applying device of 0 μA (no electric current was applied), 25 μA, 50 μA, and 75 μA.

As a result, the ratio of PI positive cells of each of the 25 μA, 50 μA, and 75 μA groups after the application of an electric current was reduced as compared to the 0 μA control group (to which no electric current was applied). That is, it was demonstrated that an anti-necrotic effect was induced by the application of an electric current.

4-2) LC3×DAPI Staining

NIH3T3 cells were grown in a chamber by the above-described culture method and costained with LC3 protein (red) expressed when necrotic protein is induced and DAPI (blue) for detecting cell nuclei.

As a result, the ratio of LC3 positive cells of each of the 25 μA, 50 μA, and 75 μA groups after the application of an electric current was reduced as compared to the 0 μA control group (to which no electric current was applied). Particularly, the ratio of LC3 positive cells of the control group was 50%, whereas it was observed that those of the 25 μA group and the 50 μA group were significantly reduced to 28% and 16%, respectively. Also in this system, it was demonstrated that an anti-necrotic effect was induced by the application of an electric current.

(5) Verification of Anti-Apoptotic Effect and Anti-Necrotic Effect by Flow Cytometry In this experiment, an anti-apoptotic effect and an anti-necrotic effect were verified by flow cytometry.

NIH3T3 cells were grown in a chamber by the above-described culture method and costained with AnnexinV (green) for detecting apoptotic cell membrane and Propidium Iodido (PI) (red) for detecting necrotic cells. The NIH3T3 cells were divided into four groups depending on different set electric current values of the electric current applying device of 0 μA (no electric current was applied), 25 μA, 50 μA, and 75 μA.

TABLE 3

| | Ratio (%) | | | |
|---|---|---|---|---|
| | Necrotic Cells | Early Apoptotic Cells | Late Apoptotic Cells | Other Cells |
| 0 μA (control) | 10.74 | 4.37 | 32.54 | 52.36 |
| 25 μA | 1.37 | 1.74 | 12.18 | 84.71 |
| 50 μA | 1.73 | 0.95 | 6.92 | 90.39 |
| 75 μA | 2.42 | 0.94 | 4.81 | 91.83 |

As a result, as shown in Table 3, the ratio of necrotic cells, the ratio of early apoptotic cells, and the ratio of late apoptotic cells of each of the 25 μA, 50 μA, and 75 μA groups were reduced as compared to the 0 μA control group (to which no electric current was applied). Therefore, it was demonstrated by flow cytometry that an anti-apoptotic effect and an anti-necrotic effect were induced by the application of an electric current.

Further, as a comparative experiment, an anti-apoptotic effect and an anti-necrotic effect were verified by flow cytometry in the same manner as described above except that the set electric current values of the electric current applying device were changed to 15 μA and 100 μA. As a result, the ratio of necrotic cells of the 15 μA or 100 μA group was comparable to that of the 0 μA control group. The ratio of apoptotic cells of the 15 μA or 100 μA group was slightly reduced, but the degree of the reduction was much smaller than those of the 25 to 75 μA groups. That is, remarkable induction of an anti-apoptotic effect and an anti-necrotic effect was not observed in the 15 μA or 100 μA group.

Each of the above experiments was performed two or more times, and the results showed the same tendency. That is, it has been confirmed that the experiments are reproducible.

INDUSTRIAL APPLICABILITY

According to the present invention, it is possible to hold a living cell while suppressing the occurrence of apoptosis or necrosis in the living cell. Particularly, it is possible to suppress the occurrence of apoptosis or necrosis in a cultured cell.

DESCRIPTION OF REFERENCE NUMERALS

1 Alternating-current voltage applying device
2 Treatment chamber (culture apparatus)
3 Stage member
4 Supporting member
5 Holder
6 Container holding a living cell
7 Electric transformer
9 Terminal
10, 11 Wiring

The invention claimed is:

1. A method for preventing one or more of an apoptosis and a necrosis in a living cell, comprising applying a sinusoidal alternating-current voltage to the living cell for 12 hours or longer so that an electric current of 25 μA or higher but 75 μA or lower flows, wherein the sinusoidal alternating-current voltage is applied to a stage member on which a container holding the living cell is placed.

2. The method according to claim 1, wherein the living cell is a cultured cell in vitro.

3. The method according to claim 1, wherein the voltage value of the alternating-current voltage is 10 V or higher but 5 kV or lower.

4. The method according to claim 2, wherein the voltage value of the alternating-current voltage is 10 V or higher but 5 kV or lower.

* * * * *